(12) United States Patent
Sambusseti et al.

(10) Patent No.: US 10,092,389 B2
(45) Date of Patent: Oct. 9, 2018

(54) ORTHOTOPIC ARTIFICIAL BLADDER ENDOPROSTHESIS

(71) Applicant: Antonio Sambusseti, Cremona (IT)

(72) Inventors: Antonio Sambusseti, Cremona (IT); Gianni Cancarini, Brescia (IT); Christian Choux, Savigneux (FR)

(73) Assignee: Antonio Sambusseti, Cremona (IT)

( * ) Notice: Subject to any disclaimer, the term of this patent is extended or adjusted under 35 U.S.C. 154(b) by 0 days.

(21) Appl. No.: 15/128,238

(22) PCT Filed: Apr. 8, 2015

(86) PCT No.: PCT/IB2015/052535
§ 371 (c)(1),
(2) Date: Sep. 22, 2016

(87) PCT Pub. No.: WO2015/159185
PCT Pub. Date: Oct. 22, 2015

(65) Prior Publication Data
US 2017/0165047 A1   Jun. 15, 2017

(30) Foreign Application Priority Data
Apr. 14, 2014 (IT) .............................. MI2014A0694

(51) Int. Cl.
*A61F 2/04* (2013.01)
*A61M 25/00* (2006.01)
(Continued)

(52) U.S. Cl.
CPC .............. *A61F 2/042* (2013.01); *A61L 27/18* (2013.01); *A61L 29/06* (2013.01); *A61L 29/103* (2013.01);
(Continued)

(58) Field of Classification Search
CPC .............. A61F 2/042; A61F 2210/0057; A61F 2230/0071; A61F 2250/0067;
(Continued)

(56) References Cited

U.S. PATENT DOCUMENTS 5,250,029 A * 10/1993 Lin .................... A61M 25/0017
604/103.11
6,048,330 A    4/2000 Atala
(Continued)

FOREIGN PATENT DOCUMENTS

DE         2655034 A1   6/1978
IT    MI20121709 A1   4/2014
(Continued)

OTHER PUBLICATIONS

International Search Report and Written Opinion dated Sep. 11, 2015 for PCT/IB2015/052535 to Antonio Sambusseti filed Apr. 8, 2015.

*Primary Examiner* — Christopher D Prone
*Assistant Examiner* — Rokhaya Diop
(74) *Attorney, Agent, or Firm* — Vorys, Sater, Seymour and Pease LLP

(57) ABSTRACT

An orthotopic artificial bladder endoprosthesis includes a casing defining an enclosure for containing the urine of a patient; the casing being made of a PGA fiber fabric; two first connectors connected to the casing and connectable to the ureters of the patient to allow the entrance of the urine into the enclosure; a second connector connected to the casing and connectable to the patient's urethra to allow the outflow of the urine from the enclosure; a catheter inserted in the enclosure through the second connector and including a duct and an expandable element in fluid communication with the duct.

20 Claims, 2 Drawing Sheets

(51) Int. Cl.
*A61L 29/06* (2006.01)
*A61L 27/18* (2006.01)
*A61L 29/10* (2006.01)
*A61M 25/10* (2013.01)

(52) U.S. Cl.
CPC .... *A61M 25/0017* (2013.01); *A61M 25/1002* (2013.01); *A61F 2210/0004* (2013.01); *A61F 2210/0057* (2013.01); *A61F 2210/0076* (2013.01); *A61F 2230/0071* (2013.01); *A61F 2250/0067* (2013.01); *A61L 2430/22* (2013.01); *A61M 25/10* (2013.01)

(58) Field of Classification Search
CPC .... A61F 2210/0076; A61F 2210/0004; A61M 25/0017; A61M 25/1002; A61L 29/103; A61L 27/18; A61L 29/06; A61L 2430/22
See application file for complete search history.

(56) References Cited

U.S. PATENT DOCUMENTS

| | | | |
|---|---|---|---|
| 9,375,306 B2 | 6/2016 | Sambusseti | |
| 2003/0229264 A1* | 12/2003 | Connors | A61F 2/0027 600/29 |
| 2007/0219488 A1 | 9/2007 | Francescatti | |
| 2007/0276507 A1* | 11/2007 | Bertram | A61F 2/042 623/23.65 |
| 2008/0319460 A1 | 12/2008 | Cortellini | |
| 2009/0036907 A1* | 2/2009 | Bayon | A61L 27/38 606/151 |
| 2011/0270409 A1* | 11/2011 | Sambusseti | A61F 2/042 623/23.65 |
| 2013/0103164 A1 | 4/2013 | Sambusseti | |
| 2013/0317622 A1 | 11/2013 | Sambusseti et al. | |
| 2014/0012394 A1 | 1/2014 | Sambusseti | |
| 2015/0030657 A1 | 1/2015 | Ludlow et al. | |
| 2015/0045907 A1 | 2/2015 | Sambusseti | |
| 2015/0223924 A1 | 8/2015 | Sambusseti | |
| 2016/0000552 A1 | 1/2016 | Sambusseti et al. | |

FOREIGN PATENT DOCUMENTS

| | | |
|---|---|---|
| TN | 2010000104 A1 | 9/2011 |
| WO | 9850100 A1 | 11/1998 |
| WO | 2007039159 A1 | 4/2007 |
| WO | 2007039160 A1 | 4/2007 |
| WO | 2007075545 A2 | 7/2007 |
| WO | 2007095193 A2 | 8/2007 |
| WO | 2009033528 A1 | 3/2009 |
| WO | 2009077047 A1 | 6/2009 |
| WO | 2010078949 A1 | 7/2010 |
| WO | 2011018300 A1 | 2/2011 |
| WO | 2011064110 A1 | 6/2011 |
| WO | 2011140137 A2 | 11/2011 |
| WO | 2011160875 A1 | 12/2011 |
| WO | 2012123272 A1 | 9/2012 |
| WO | 2013135543 A1 | 9/2013 |
| WO | 2013135544 A1 | 9/2013 |
| WO | 2014045190 A1 | 3/2014 |
| WO | 2014057444 A1 | 4/2014 |
| WO | 2015071472 A1 | 5/2015 |
| WO | 2015087250 A1 | 6/2015 |
| WO | 2015159185 A1 | 10/2015 |
| WO | 2016051330 A1 | 4/2016 |
| WO | 2016051333 A1 | 4/2016 |
| WO | 2016071290 A1 | 5/2016 |

* cited by examiner

ORTHOTOPIC ARTIFICIAL BLADDER ENDOPROSTHESIS

CROSS-REFERENCE TO RELATED APPLICATIONS

This is a § 371 National Stage Application of International Application No. PCT/IB2015/052535 filed on Apr. 8, 2015, claiming the priority of Italian Patent Application no. MI2014A000694 filed on Apr. 14, 2014.

FIELD OF THE INVENTION

The present invention relates to an orthotopic artificial bladder endoprosthesis.

The application of the present invention lies in the replacement of the bladder of a patient, if the latter is suffering from serious incurable diseases such to compromise the correct function thereof.

BACKGROUND OF THE INVENTION

Known bladder endoprostheses comprise a balloon casing made with an impermeable layered silicone membrane.

Such casing is sufficiently rigid so as to stably keep its shape and flexible to be able to be manually compressed to ensure that it empties.

The casing has a connection element located at a lower portion of the casing to connect with the patient's urethra. Similarly, two connection bodies are located at the top to enable connection with the ureters.

These connections are achieved by suturing or by simply interlocking.

Following the implant of the endoprosthesis in the patient, there is the formation of a musculo-fibrous tissue layer (not impermeable) around the casing. In such a manner, a neobladder is generated around the endoprosthesis.

Since the endoprostheses of known type are permanent, complications can occur even after the complete rehabilitation of the patient.

Indeed, it may occur that an infection hits the neobladder in an accidental manner or following the use of catheters.

In such case, a suitable antibiotic treatment is necessary. Such drugs are effective in extinguishing the bacterial loads nested in biological tissue and have poor or even zero effect on bacterial loads nested on artificial materials like those that make up the casing. Disadvantageously, therefore, endoprostheses of known type can represent an obstacle to the effectiveness of antibiotic treatments.

Other solutions of bladder endoprosthesis are disclosed in WO2011/140137 which describes a matrix or scaffold, rigid or flexible and having a substantially round or scalloped or star shaped shape suitable to define, when implanted, the shape of bladder, with said matrix or scaffold used for the reconstruction of a bladder and such that, after the biodegradation of said matrix or scaffold, the reconstructed bladder works in a fashion similar to a natural bladder.

Another known solution is disclosed in WO2007/095193 which describes a scaffold suitable for organ reconstruction and augmentation and, in particular, it discloses a method and the materials for tissue and organs reconstruction, repair, augmentation and replacement, said material suitable to be used with patient having defect in urogenital tissues or organs; furthermore, it is disclosed an embodiment wherein the artificial bladder comprises hemispherical portions or valves symmetrical one with respect to the other and wherein said portions comprises external flanges suitable for manipulating the portions prior or during the surgery and to allow the sealing of said two portions.

The document MI2012A001709 discloses an endoprosthesis of artificial bladder which comprises a multilayered enclosure having a balloon shape and which is sufficiently rigid to keep its shape during the reconstruction process.

Another known document, WO98/50100, discloses a system and a method for promoting the growth or the expansion of biological tissue and, more in particular, it teaches the use of a device for seeding fluid under pressure in a balloon inserted in a interstitial cavity of the human body so as to allow a tissue expansion of said interstitial cavity suffering from pathology such as a bladder having an insufficient volume/capacity or where it is required perform an expansion of the urethra or similar.

Another known solution is disclosed in WO2007/075545, which discloses the use of an expandable balloon suitable to perform a drainage of a cavity wherein said balloon is inserted.

All said known solutions are complex not only under the constructional point of view but they are also complex considering the process and method on implantation.

SUMMARY OF THE INVENTION

In this context, the technical task underlying the present invention is to propose an orthotopic artificial bladder endoprosthesis that overcomes the drawback of the abovementioned prior art.

In particular, the object of the present invention is to provide an orthotopic artificial bladder endoprosthesis that limits the risks associated with bacterial infections.

The specified technical task and the specified object are substantially achieved by an orthotopic artificial bladder endoprosthesis comprising the technical characteristics set forth in one or more of the enclosed claims.

BRIEF DESCRIPTION OF THE DRAWING

Further characteristics and advantages of the present invention will emerge more clearly from the following non-limiting description of a preferred but not exclusive embodiment of an orthotopic artificial bladder endoprosthesis, as illustrated in the enclosed drawings in which.

DETAILED DESCRIPTION OF THE PREFERRED EMBODIMENTS

Figure 1:
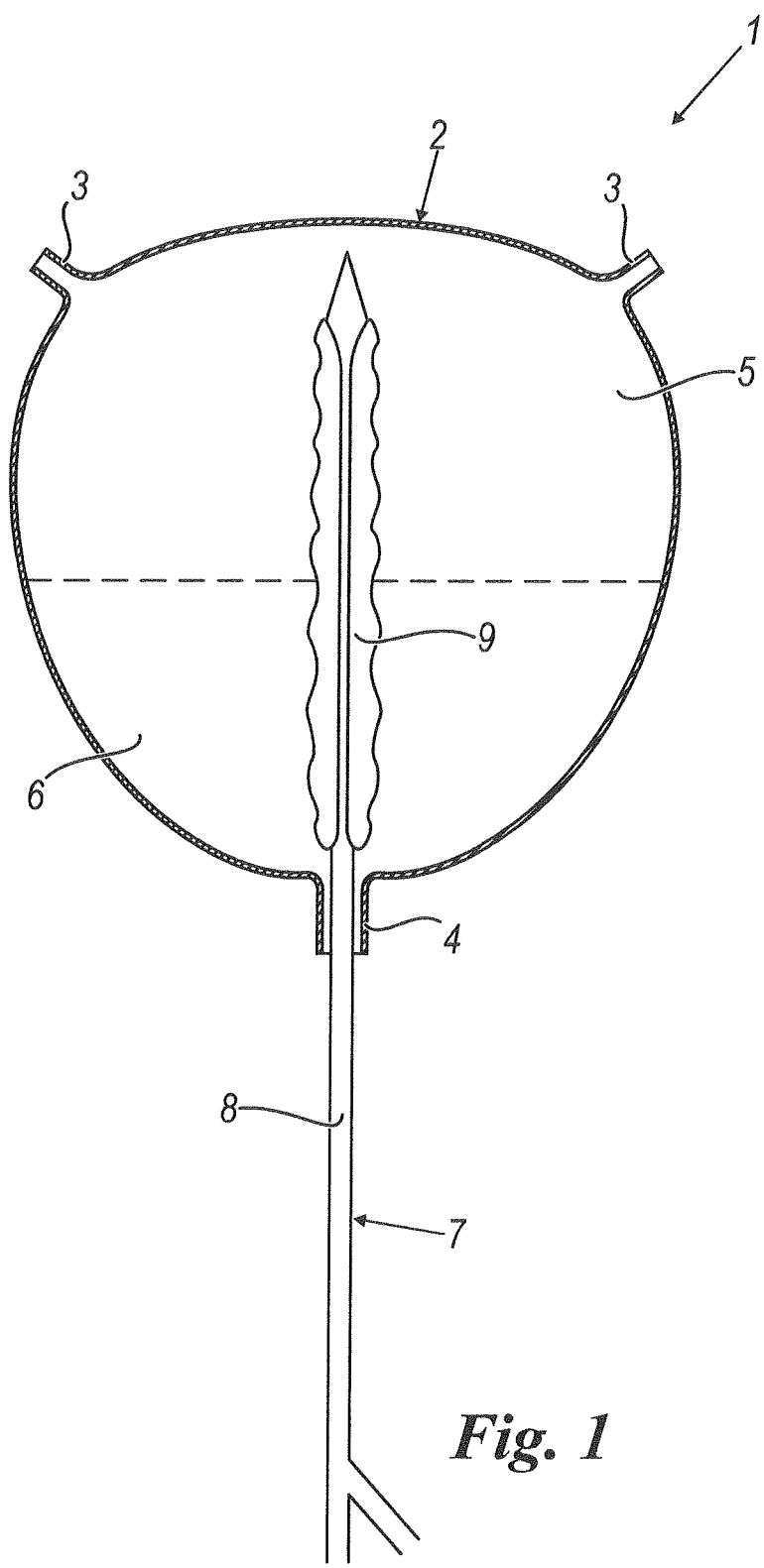
FIG. 1 is a schematic view of an orthotopic artificial bladder endoprosthesis in accordance with the present invention in a first configuration.

With reference to the enclosed figures, reference number 1 overall indicates an orthotopic artificial bladder endoprosthesis in accordance with the present invention. According to that illustrated, the endoprosthesis 1 comprises a casing 2 which, at its interior, defines an enclosure for containing urine.

Two first connectors 3 are connected to the casing 2 in a manner so as to be able to connect the ureters of the patient to the casing 2 and allow the urine, coming from the kidneys, to flow into the enclosure.

Analogously, a second connector 4 is connected to the casing 2 in a manner so as to be able to connect the patient's urethra to the casing 2 and allow the urine to exit from the enclosure.

The casing 2 has substantially spherical shape.

In greater detail, the casing 2 comprises two hemispherical caps 5,6 which are connected, e.g. by means of sewing, to each other at respective edges.

Preferably, the casing 2 is obtained by using an ultra-light thread or monofilament deriving from preferably homopolymer PGA (polyglycolide or poylglycolic acid) fibers. PGA is a highly biocompatible and resorbable polymer and resistant to urine. Specifically, the resorption time of PGA is approximately one month.

Advantageously, the use of PGA fibers in obtaining the fabric of the casing 2 allows the formation of the musculofibrous tissue during the resorption phase of the endoprosthesis 1.

In addition, always during resorption, there is the formation of a transition epithelium layer, which is also called urothelium. Advantageously, the layer of urothelium is impermeable, an essential fact to ensure the correct functioning of the prosthesis and the neobladder that is being formed.

Furthermore, once the endoprosthesis 1 is inserted, the fabric of the casing 2 is impregnated with blood and in particular with plasma, which allows the antibiotic drugs to be effective on the endoprosthesis.

The fabric of the casing 2 can be obtained by weaving the PGA thread in various ways, giving rise to a knitted fabric, a woven fabric or a non-woven fabric.

Preferably, the fabric is a knitted fabric, still more preferably a warp knitted fabric.

In this case, the fabric has a rougher surface capable of assuming a net configuration with sufficiently small meshes.

In detail, its weft is such that its interstitial space is less than 200 μm, preferably around 160 μm, corresponding to an average area of the holes equal to approximately 0.02 mm². This ensures impermeability to urine, preventing leaks.

Furthermore, the fabric is preferably textured so as to give it even greater surface roughness and greater rigidity and impermeability. The greater roughness of the fabric limits the risk of adhesion of the fibrous capsule.

Purely by way of example, the fabric has a thickness substantially comprised between 0.3 mm and 0.6 mm, more preferably comprised between 0.4 mm and 0.53 mm, still more preferably being substantially 0.45 mm.

By way of example, the casing 2 has a volume comprised between 250 cm³ and 625 cm³. It should be considered that typically, during use, the volume of the casing 2 is on average reduced by 20% once implanted.

The endoprosthesis 1 also comprises a catheter 7 inserted in the enclosure of the casing 2.

The catheter 7 is preferably of Foley type.

This comprises a duct 8 and an expandable element 9 (or balloon) connected in proximity to a free end of the duct 8.

Figure 2:
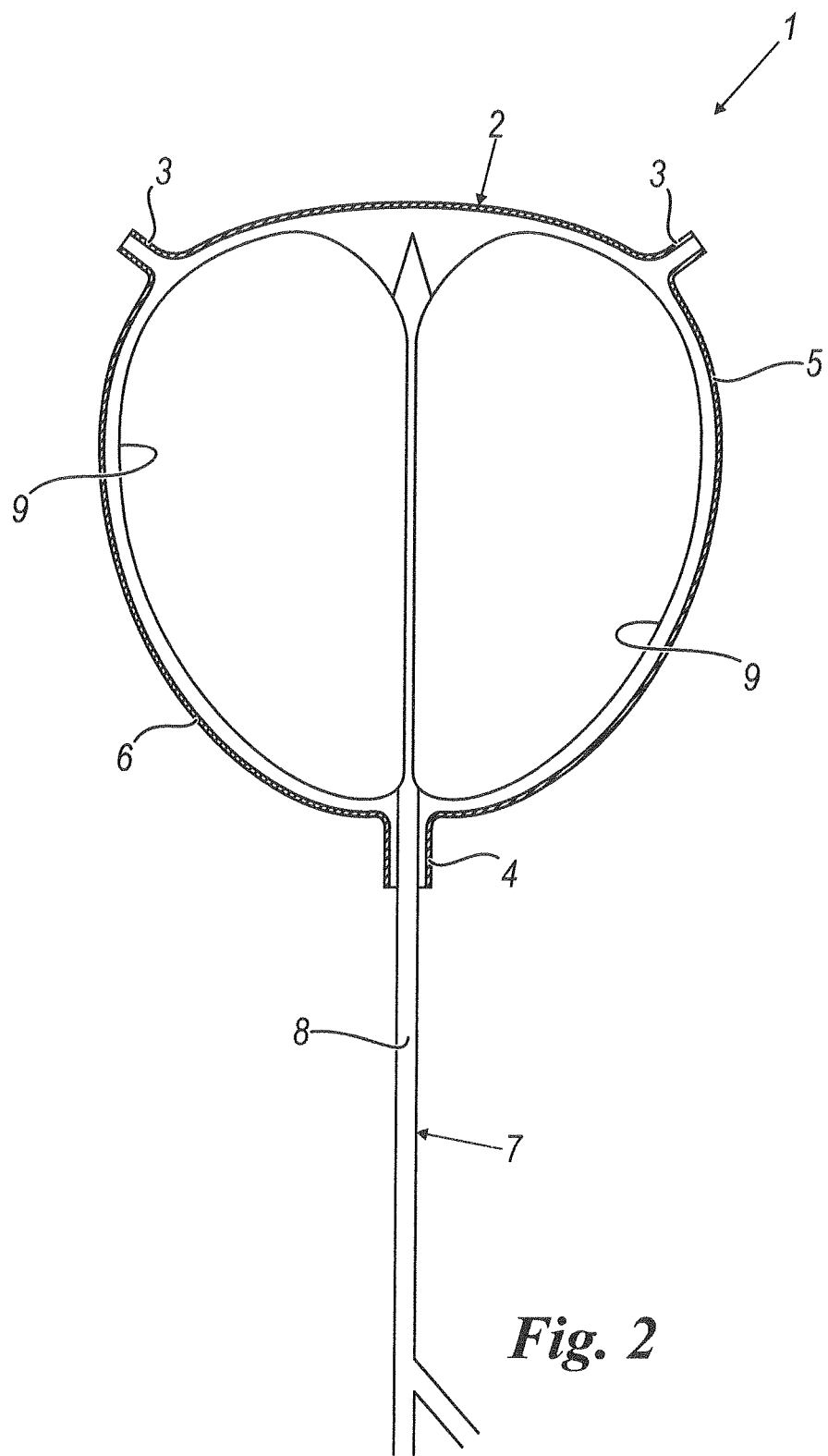
FIG. 2 is a schematic view of the orthotopic artificial bladder endoprosthesis of FIG. 1 in a second configuration.

The duct 8 is in fluid communication with the expandable element 9. In such a manner, by introducing a fluid into the expandable element 9, this is expanded (FIG. 2). In parallel, by suctioning the fluid, the expandable element 9 is deflated (FIG. 1).

The expandable element 9 has, at a completely extended configuration, a volume comprised between 200 cm³ and 500 cm³.

It is observed that the known catheters of Foley type have expandable elements with maximum capacity not greater than 120 cm³.

During use (and as will be clearer hereinbelow), when the catheter 7 is inserted in the enclosure of the casing 2, a fluid (e.g. physiological solution) is introduced through the duct 8 into the expandable element 9 which, being widened, widens and sustains the casing.

In detail, the expandable element 9 can stably assume, during use, any volume up to the maximum volume. In this manner, the expandable element 9 can support casings 2 of any size. Indeed, the casing 2 has a size dependent on the size of the bladder to be replaced, which can vary depending on the age and sex of the patient.

The catheter 7 can be made of silicone, latex, silicone covered with latex or even polyurethane.

Preferably, in the described embodiment, the catheter 7 is made of polyurethane.

In each case, the catheter 7 is covered, at least externally, with a layer of highly biocompatible protection material. By way of example, such material is turbostratic pyrolytic carbon with a thickness comprised between 0.2 μm and 0.3 μm.

The layer of turbostratic pyrolytic carbon allows facilitating the regeneration of the tissue at the junction point between the urethra and the PGA casing 2.

It should be specified that the layer of turbostratic pyrolytic carbon covers both the duct 8 and the expandable element 9 of the catheter 7.

Preferably, the free end of the duct 8 of the catheter 7 is shaped obliquely.

The catheter 7 is preferably a two-way catheter. In such a manner, the entrance and exit of the fluid from the expandable element 8 is allowed.

The catheter 7 can also be a three-way catheter. In such case, the third pathway allows directly introducing medicinal substances into the enclosure of the casing 2, through the free end of the duct 8 of the catheter, such medicinal substances including for example antibiotics.

The endoprosthesis 1 can be arranged in kit form, in which the catheter 7 is separate from the casing 2 and is insertable therein.

In an alternative embodiment, the endoprosthesis 1 comprises a single casing 2 and two catheters 7.

From an operative standpoint, when the endoprosthesis 1 must be implanted, it is positioned in the pelvis of the patient after the removal of the natural bladder.

The endoprosthesis 1 is inserted with the catheter 7 extracted from the casing 2 and with the casing 2 flaccid.

The casing 2 is connected to the ureters of the patient, suturing them to the first connectors 4 with absorbable suture, for example of Vicryl type.

Subsequently, the catheter 7 is inserted in the patient's urethra, naturally with the extendable element 8 deflated.

Once the catheter 7 exits from the urethra in the operating field, it is inserted in the casing 2 through the second connector 5.

Only after this step, the patient's urethra is connected to the second connector 5 of the casing 2, suturing it with absorbable suture, for example of Vicryl type.

Once this connection step is completed, physiological solution is injected into the catheter 7. In particular, the physiological solution is introduced into the duct 8 up to the extendable element 9, in order to inflate it.

In detail, the extendable element 9 is inflated up to the maximum extension configuration.

This step of extending the catheter 7 is executed with open operating field in order to allow directly viewing the operation.

Indeed, the surgeon verifies that the extendable element 9 adheres inside the casing 2 in order to render the latter round or rounded.

At this point, it is possible to close the operating field once again.

As mentioned above, it is clear that the inflated extendable element 9 inside the casing 2 has the function of supporting the casing 2 itself during the period of formation of the musculo-fibrous tissue during resorption step.

Once such musculo-fibrous tissue has stably grown, it is possible to remove the catheter 7 by extracting the physiological solution from the extendable element 9, then deflating it, and removing it from the urethra.

If the kit comprises two catheters 7, it is advantageously possible to replace one catheter 7 with the other in an intermediate step during the period of resorption of the casing 2.

By way of example, the first catheter can be replaced with the second from the twentieth to the twenty-fifth day from the implant of the endoprosthesis 1. The second catheter 7 can be definitively removed between the fortieth and the fiftieth day from the implant of the endoprosthesis 1.

During use, during the regeneration follow-up period, the expandable element 9 is kept completely inflated for about ten days. Subsequently, for a period of about three days, it is partially inflated in order to allow the formation of a space between the expandable element 9 and the neobladder being formed. The evacuation of the urine is thus facilitated, allowing the kidneys to empty themselves. The brief time in which the expandable element 9 is partially deflated does not jeopardize its structural function nor allow the neobladder to collapse. Such temporary, partial deflation operation of the expandable element 9 is repeated every fifteen days for a period of about five months.

Considering that the resorption period of the casing 2 is about one month, it is observed that the temporary, partial deflation operation of the expandable element is extended for further four months. This in order to avoid the risk that the neobladder, even if completely formed, collapses and closes on itself.

During this follow-up step, it is necessary to change the Foley catheter 7 at least every fifteen days with a new and sterile Foley catheter. The invention thus described attains the pre-established object.

Indeed, the above-described endoprosthesis does not require suitable permanent support structures.

Consequently, the chances that the bacterial load can migrate inward, causing post-operating infections and complications, are reduced or eliminated.

Also the effectiveness of antibiotics is increased, since after the removal of the catheter such antibiotics operate directly on biological tissue.

The invention claimed is:

1. An orthotopic artificial bladder endoprosthesis comprising:
    a casing defining an enclosure for containing urine of a patient, said casing being made of a polyglycolic acid fiber fabric;
    two first connectors connected to the casing and connectable to two ureters of the patient to allow an entrance of urine into the enclosure;
    a second connector connected to the casing and connectable to a urethra of the patient to allow an outflow of urine from the enclosure; and
    an insert member comprising a catheter inserted in the enclosure through said second connector and comprising a duct for insertion into the enclosure and an expandable element for insertion into the enclosure in fluid communication with said single duct, the catheter duct having an open proximal end external to the casing and a closed distal end inserted into the enclosure, wherein the duct is in fluid communication with the expandable element proximal to the distal end, such that a portion of the member is within the enclosure and a portion of the member is outside the enclosure, wherein the portion of the insert member within the enclosure is only in fluid communication with the expandable element;
    wherein said expandable element has, at a completely extended configuration, a volume between 200 cm$^3$ and 500 cm$^3$, the expandable element being configured to widen for adhering to the casing and supporting the casing during a formation of musculo-fibrous tissue during a resorption step.

2. The endoprosthesis according to claim 1, wherein said catheter is a Foley catheter, wherein the casing is flaccid.

3. The endoprosthesis according to claim 1, wherein the expandable element of the catheter is made of polyurethane.

4. The endoprosthesis according to claim 1, wherein said catheter is externally covered with a layer of turbostratic pyrolytic carbon.

5. The endoprosthesis according to claim 1, wherein said catheter comprises a free end having an oblique shape.

6. The endoprosthesis according to claim 1, wherein the expandable element is configurable to assume any predetermined volume up to a maximum volume of the enclosure, the insert member consisting of at least one said catheter and the expandable element.

7. The endoprosthesis according to claim 1, wherein said casing has a substantially spherical shape.

8. The endoprosthesis according to claim 1, wherein said catheter is a three-way catheter capable of filling and emptying the expandable element and bringing liquids inside the enclosure.

9. The endoprosthesis according to claim 1, wherein said casing comprises two hemispherical caps connected together at an edge thereof.

10. The endoprosthesis according to claim 1, wherein the fabric of said casing is a warp knitted fabric.

11. The endoprosthesis according to claim 1, wherein the fabric of said casing is textured.

12. The endoprosthesis according to claim 1, wherein the fabric of said casing is a warp knitted fabric and textured.

13. The endoprosthesis according to claim 1, wherein said catheter is a Foley catheter, wherein the casing is flaccid.

14. An orthotopic artificial bladder endoprosthesis kit comprising:
    a casing defining an enclosure for containing urine of a patient, said casing being made of a polyglycolic acid fiber fabric;
    two first connectors connected to the casing and connectable to two ureters of a patient to allow an entrance of urine into the enclosure;
    a second connector connected to the casing and connectable to a urethra of the patient to allow an outflow of urine from the enclosure; and
    an insert member comprising at least one catheter insertable in the enclosure through said second connector and comprising a single duct for insertion into the enclosure and an expandable element for insertion into the enclosure in fluid communication with said single duct and suitable to widen for adhering to the casing and supporting the casing during a formation of musculo-fibrous tissue during a resorption step, the catheter duct having an open proximal end external to the casing and a closed distal end inserted into the enclosure, wherein the duct is in fluid communication with the expandable element proximal to the distal end, such that a portion of the member is within the enclosure and a portion of the member is outside the enclosure, wherein the portion of the insert member within the enclosure is only in fluid communication with the expandable element; wherein said expandable element has, at a completely extended configuration, a volume between 200 cm$^3$ and 500 cm$^3$.

15. The kit according to claim 14, wherein the expandable element of the catheter is made of polyurethane.

16. The kit according to claim 14, wherein said catheter is externally covered with a layer of turbostratic pyrolytic carbon.

17. The kit according to claim 14, wherein said catheter comprises a free end having an oblique shape.

18. The kit according to claim 14, wherein the expandable element is configurable to assume any predetermined volume up to a maximum volume of the enclosure, the insert member consisting of at least one said catheter and the expandable element.

19. The kit according to claim 14, wherein said casing has a substantially spherical shape.

20. The kit according to claim 14, wherein said catheter is a three-way catheter capable of filling and emptying the expandable element and bringing liquids inside the enclosure.

* * * * *